United States Patent [19]

Schiehser et al.

[11] Patent Number: 4,595,757
[45] Date of Patent: Jun. 17, 1986

[54] N-ALKYLATED BENZO- AND HETERO-FUSED ANTISECRETORY AGENTS

[75] Inventors: Guy A. Schiehser, Malvern, Pa.; Susan T. Nielsen, Wilmington, Del.; Donald P. Strike, St. Davids, Pa.

[73] Assignee: American Home Products Corporation, New York, N.Y.

[21] Appl. No.: 681,169

[22] Filed: Dec. 13, 1984

[51] Int. Cl.⁴ ................ C07D 513/04; C07D 417/12; C07D 405/12
[52] U.S. Cl. .................... 546/197; 546/198; 546/200; 546/232; 546/235
[58] Field of Search ............... 546/235, 197, 198, 200

[56]  References Cited
U.S. PATENT DOCUMENTS 4,390,701  6/1983  Algieri et al. ............. 546/235
4,490,527  12/1984  Schiehser et al. ........... 546/200 X

*Primary Examiner*—Richard A. Schwartz
*Attorney, Agent, or Firm*—George Tarnowski

[57] ABSTRACT

Compounds of the formula

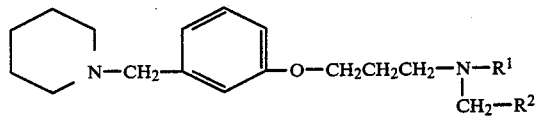

wherein R¹ is

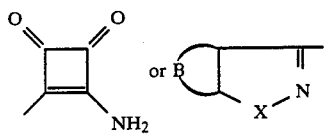

wherein B is a moiety having the formula

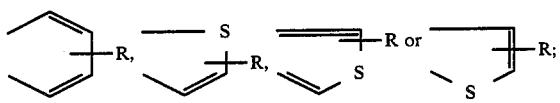

R is H, mono- or dihalo, amino, nitro, cyano, hydroxy, trifluoromethyl, mercapto, lower alkyl, lower alkoxy, alkanoyl, lowercycloalkyl, carboxy, alkoxycarbonyl, mono- or di-lower alkyl substituted amino, alkanoylamino, lower alkyl thio, loweralkylsulfonyl, sulfamoyl, lower alkyl substituted sulfamoyl, phenyl or phenyl substituted with halo, lower alkyl, lower alkoxy, trifluoromethyl, hydroxy, amino, cyano or nitro;
X is $SO_2$, SO, S or C=O; and
R² is phenyl or 1,3-benzodioxol-5-yl;
and the pharmacologically acceptable salts thereof, which are ($H^+ + K^+$)ATPase inhibitors exhibiting a cytoprotective action, are useful in the treatment of conditions where there is hypersecretion of gastric acid, such as gastric and peptic ulceration, as well as in conditions such as stress ulceration.

5 Claims, No Drawings

N-ALKYLATED BENZO- AND HETERO-FUSED ANTISECRETORY AGENTS

The present invention relates to novel compounds possessing $(H^+ +K^+)$ATPase inhibitory activity which are useful as antisecretory/antiulcer agents.

Antisecretory agents useful in the treatment of peptic ulcer disease fall into several categories. Cholinergic antagonists, such as the natural and synthetic belladonna alkaloids, have been long used in the treatment of peptic ulcer disease. A more recent development in the treatment of peptic ulcer disease has been the discovery of a large class of histaminergic antagonists. It has been found that the physiologically active compound histamine, which occurs naturally within the animal body, is able to combine, in the course of exerting its activity, with certain specific receptors of which there are at least two distinct and separate types. The first has been named the $H_1$ receptor (Ash and Schild, Brit. J. Pharmac., 1966, 27,427) and the action of histamine at this receptor is blocked (antagonized) by classical "antihistamine" drugs such as mepyramine (pyrilamine). The second histamine receptor has been named the $H_2$ receptor (Black et al., Nature, 1972, 236, 385) and the action of histamine at this receptor is blocked by drugs such as cimetidine. It is known that one of the results of the blockage of the action of histamine at the $H_2$ receptor is the inhibition of the secretion of gastric acid and a compound which possesses this ability is therefore useful in the treatment of peptic ulcers and other conditions caused or exacerbated by gastric acidity, including stress ulcers and gastrointestinal bleeding due to trauma.

The most recent development in antisecretory/antiulcer research has been the discovery of yet a new approach to the inhibition of gastric acid secretion. The enzyme $(H^+ +K^+)$ATPase is one of several that are found in gastric cells. $(H^+ +K^+)$ATPase occurs only at the secretory surface of the parietal cells of the gastric mucosa and functions to catalyze the exchange of protons and potassium ions. This enzyme is considered to be the "proton pump" responsible for gastric acid secretion. Accordingly, inhibition at this point in the production of gastric acid secretion affords a very selective antisecretory agent. At the present time, the compound omeprazole:

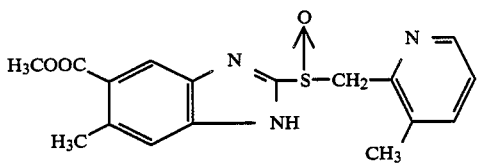

is considered to be the leading entity in a new class of antisecretory agents. $(H^+ +K^+)$ATPase inhibitors differ from the $H_2$-receptor antagonists by the locus of their action. Thus, for example, isolated guinea pig gastric mucosa can be stimulated by dibutyryl cyclic AMP after pretreatment with theophylline [Sjostrand et al., Acta Physiol. Scand., Symp. Gastric Ion Transport, (Spec. Suppl.) 181-186 (1978)], and such stimulated secretion can be inhibited by omeprazole [Olbe et al., Scand. J. Gastroenterol., 14 (Suppl. 55) 131-132 (1979)] while $H_2$-receptor antagonists have no such action.

In an additional study [Fellenius, Nature 220, 159-160 (1981)], it was found that as among atropine, cimetidine and omeprazole, only omeprazole inhibited proton transport by the inhibition of $(H^+ +K^+)$ATPase, while both atropine and cimetidine were devoid of this activity. Cimetidine was found to inhibit only those gastric secretions which were agonized by histamine, indicating that cimetidine and similar $H_2$-receptor antagonists act at a site of action remote from the $(H^+ +K^+)$ATPase site of action.

Among the many $H_2$-receptor antagonists now known are those disclosed in U.S. Pat. No. 4,490,527 and having the general structure

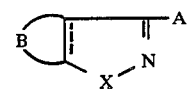

wherein B is a moiety having the formula

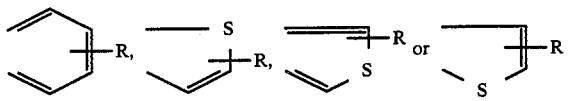

and A is an amine having the formula

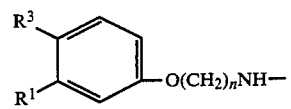

wherein n=1–4. Also disclosed in U.S. Pat. No. 4,390,701, is an $H_2$-receptor antagonist having the formula

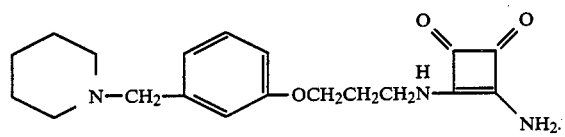

These compounds are potent $H_2$-receptor antagonists exhibiting activities substantially greater than cimetidine. It has now been found that these compounds and other known $H_2$-receptor antagonists can be structurally modified to produce compounds which exhibit $(H^+ +K^+)$ATPase inhibitory activity instead of $H_2$-receptor antagonist activity.

Accordingly, the present invention provides a novel group of compounds, with $(H^+ +K^+)$ATPase inhibitory activity, having the following formula

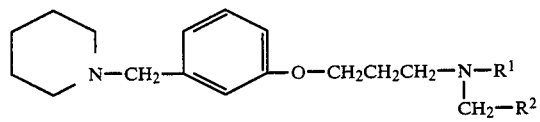

wherein $R^1$ is

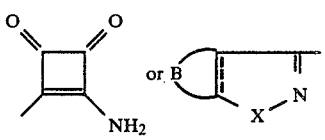 or 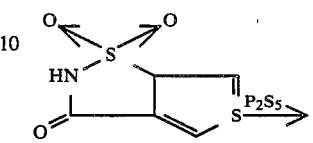

wherein B is a moiety having the formula

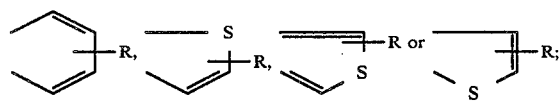

R is mono- or dihalo, amino, nitro, cyano, hydroxy, trifuoromethyl, mercapto, lower alkyl, lower alkoxy, alkanoyl, lowercycloalkyl, carboxy, alkoxycarbonyl, mono- or di-lower alkyl substituted amino, alkanoylamino, lower alkyl thio, loweralkylsulfonyl, sulfamoyl, lower alkyl substituted sulfamoyl, phenyl or phenyl substituted with halo, lower alkyl, lower alkoxy, trifluoromethyl, hydroxy, amino, cyano or nitro;

X is $SO_2$, SO, S or C=O; and $R^2$ is phenyl or 1,3-benzodioxol-5-yl;

and the pharmacologically acceptable salts thereof.

The term "halo" refers to fluoro, chloro and bromo. The terms "lower alkyl" and "lower alkoxy" refer to moieties having 1 to 6 carbon atoms in the carbon chain. The term "lower cycloalkyl" refers to cyclic structures having 5 to 7 carbon atoms. The term "alkanoyl" refers to the moiety RCO— wherein R is an alkyl group having 1 to 4 carbon atoms.

The compounds of the invention can be readily prepared by reacting the chloride of an appropriate benzisothiazole or a derivative thereof, a 3-(methylthio)-thienoisothiazole-1,1-dioxide or an appropriate derivative thereof or a suitable squaric acid derivative with the desired amine according to the following reaction sequence.

$R^1$ +

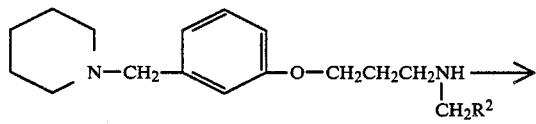

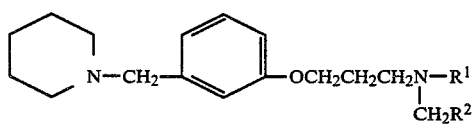

where B, X, $R^1$ and $R^2$ are as defined hereinbefore. The benzisothiazole chlorides are known compounds which are readily available or which can be prepared by known methods. Thus, for example, the compound

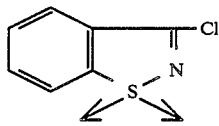

is pseudo saccharin chloride, and can be prepared according to the method of Stephen et al., *J. Chem. Soc.,* 1957, 490–92. The 3-(methylthio)thienoisothiazoles can be prepared according to the following reaction sequence exemplified for 3-(methylthio)thieno[3,4-d]isothiazole-1,1-dioxide:

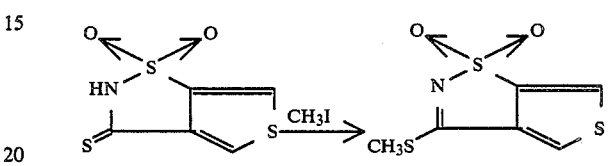

The starting compound thieno[3,4-d]isothiazol-3(2H)-one-1,1-dioxide can be prepared according to the procedure of P. A. Rossy et al., *J. Org. Chem.,* 45, 617 (1980).

The starting compound squaric acid, which is 3,4-dihydroxy-3-cyclobutane-1,2-dione:

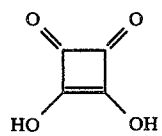

is a commercially available compound.

The amines having the formula

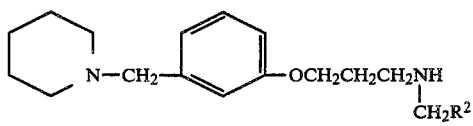

can be prepared in the following manner:

$R^2CHO \longrightarrow$

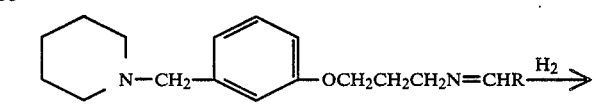

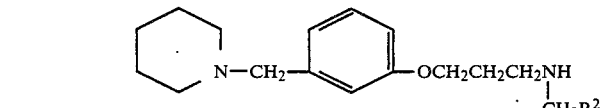

where $R^2$ is as defined hereinbefore. The starting primary amine

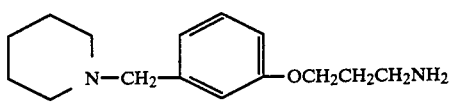

is disclosed in U.K. Pat. No. 2,023,133 and it can be prepared according to the following reaction sequence:

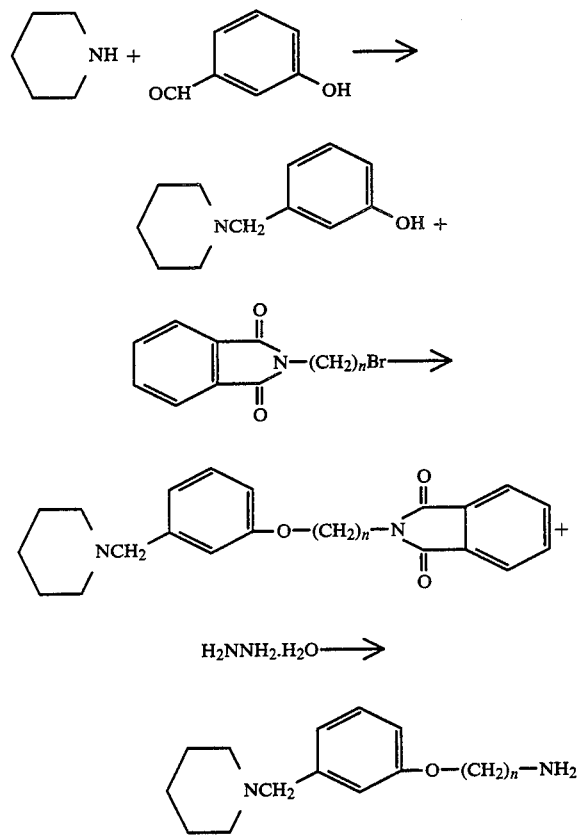

As an alternative procedure, the preparation of the isoindoledione reactant can be carried out as follows:

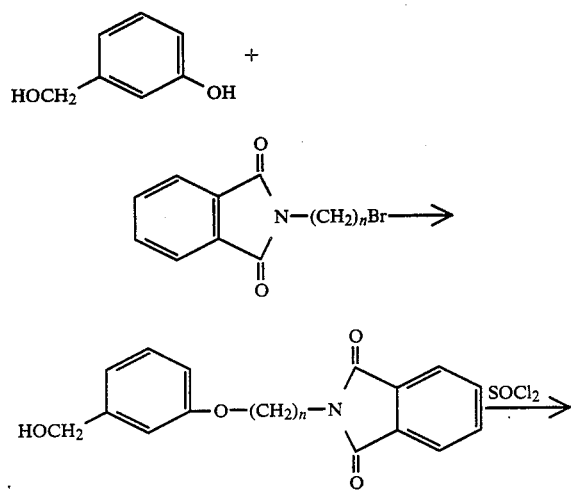

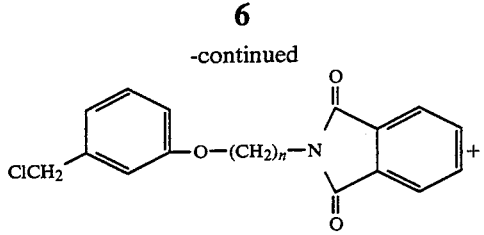

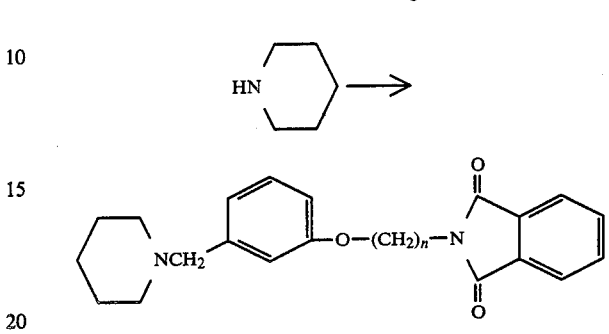

The compounds of the invention readily form pharmacologically acceptable salts with both inorganic and organic acids, such as hydrochloric, hydrobromic, sulfuric, nitric, phosphoric, acetic, maleic, fumaric, citric, oxalic and the like.

The compounds of the invention exhibit $(H^+ + K^+)$ATPase inhibitory activity and can be used in the treatment of conditions where there is hypersecretion of gastric acid, such as in gastric and peptic ulceration, and other conditions caused or exacerbated by gastric acidity such as stress ulceration or gastric intestinal bleeding due to trauma. It is significant to not that the compounds of the invention, as a result of modification of the basic molecule by N-benzylation/benzodioxolation, are transformed into $(H^+ + K^+)$ATPase inhibitors, losing their activity as $H_2$-receptor antagonists. Additionally, and equally significant, is the fact that the compounds of the invention exhibit the capability of ameliorating ulcerogenesis, thereby having the further valuable property of being cytoprotective.

The compounds of the invention can be administered orally or parenterally or by suppository, of which the preferred route is the oral route. They may be used in the form of the base or as a pharmacologically acceptable salt. They will in general be associated with a pharmaceutically acceptable carrier or diluent, to provide a pharmaceutical composition.

The compounds of the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form.

A convenient daily dose by the oral route would be of the order of 100 mg to 1.2 g per day, in the form of dosage units containing from 20 to 200 mg per dosage unit. A convenient regimen in the case of a slow release tablet would be twice or three times a day.

Parenteral administration may be by injections at intervals or as a continuous infusion. Injection solutions may contain from 10 to 100 mg/ml of active ingredient.

The $(H^+ + K^+)$ATPase inhibitory activity of the compounds of the invention may be demonstrated by the ability of the compounds to inhibit the dibutyryl cyclic AMP-stimulated $^{14}C$-aminopyrine uptake by rat mucosal cells. The antisecretory activity of the compounds may be demonstrated by activity in other more generalized procedures, such as the modified Shay procedure of pylorus ligation for the study of rat gastric secretion. The cytoprotective capability of the compounds of the invention may be demonstrated by activity in the cold/restraint stress induced ulceration assay. The lack of $H_2$-receptor antagonist properties of the compounds of the invention may be demonstrated by the inactivity of the compounds in inhibiting the histamine-induced positive chronotropic response in the spontaneously beating right atrium of the guinea pig heart. The procedures for these tests and the results for some of the compounds of the invention are presented at the end of the following examples, which will serve to illustrate the present invention.

PREPARATION A

Preparation of 3-Chlorobenzisothiazole-1,1-Dioxide (ψ-Saccharin Chloride)

Following the procedure of Stephen et al., *J. Chem. Soc.*, 1957,490–92, 1 mol of saccharin (1,2-benzisothiazol-3(2H)-one 1,1-dioxide) is heated with 1.1 mol phosphorus pentachloride at 170° C. for 1.5 hours. Phosphorus oxychloride is removed at 60°/30 mm and the yellow crystalline residue of ψ-saccharin chloride and o-cyanobenzene sulfonyl chloride is treated with ether in which the latter is soluble. The sparingly soluble ψ-saccharin chloride in a yield of 28% is collected and crystallized from ether as white needles, m.p. 132°–137° C.

PREPARATION B

Preparation of 3-(Methylthio)Thieno-[3,4-d]Isothiazole 1,1-Dioxide

A. Thieno[3,4-d]Isothiazol-3(2H)-Thione 1,1-Dioxide

To a mixture of 5.6 g (0.03 mole) of thieno[3,4-d]isothiazol-3(2H)-one1,1-dioxide in 50 ml of dry pyridine is added 5.6 g (0.016 mole) of phosphorus pentasulfide portionwise over 3 minutes. The viscous mixture is slowly heated in an oil bath under an atmosphere of nitrogen. The temperature of the oil bath is slowly increased to 80° C. after 30 minutes. The temperature of the oil bath is then kept at 80° C. for 25 minutes, the internal temperature reading 63° C. The solution is cooled to 50° C. and is added dropwise over 5 minutes to 200 ml of water and cooled in an ice bath. The precipitate which forms is collected and discarded. The filtrate is cooled in ice and acidified with concentrated hydrochloric acid to pH 1. The precipitate which forms is collected to yield 40% of material. In another experiment, a sample is recrystallized from water to obtain an analytical sample, m.p. 196°–8° C. (dec.).

Analysis for: $C_5H_3NO_2S_3$: Calculated: C, 29.26; H, 1.47; N, 6.82. Found: C, 29.91; H, 1.43; N, 6.87.

B. 3-(Methylthio)Thieno[3,4-d]Isothiazole 1,1-Dioxide

To a mixture of 0.9 g (0.0044 mole) of thieno[3,4-d]isothiazol-3(2H)-thione 1,1-dioxide in 4 ml of ethanol is added a solution of 0.35 g (0.0044 mole) of 50% sodium hydroxide in 3 ml of water. To this thick mixture is added 0.62 g (0.0044 mole) of iodomethane. The mixture is heated under reflux for 5 minutes, and then filtered to give 0.35 g of product. On cooling, a second crop of 0.1 g of material is obtained. A small amount of the first crop is recrystallized from ethanol to afford an analytical sample, m.p. 184°–6° C.

Analysis for: $C_6H_5NO_2S_3$: Calculated: C, 32.86; H, 2.30; N, 6.39. Found: C, 32.76; H, 2.27; N, 6.43.

EXAMPLE 1

A.

N-[3-[3-(1-piperidinylmethyl)phenoxy]propyl]benzenemethanamine ethandioate (1:2)

A mixture of 10.0 g (40 mmol) of 3-[3-[(1-piperidinyl)methyl]phenoxy]propylamine and 4.24 g (40 mmol) of benzaldehyde in 120 ml of benzene is heated to reflux in a Dean-Stark apparatus and maintained for 3 hours. Rotoevaporation gives crude imine which is dissolved in ethanol, treated with 500 mg of 10% palladium on carbon, and hydrogenated at 40 psi in a Parr apparatus. When the uptake of hydrogen has ceased, the mixture is filtered through Celite and rotoevaporated to afford the free base of the title compound.

A portion of the obtained free base is treated with ethanolic oxalic acid to afford crude salt which is reconverted to the free base by partitioning between aqueous sodium hydroxide and ethyl acetate. The organic extract is dried, rotoevaporated, and treated with ethanolic oxalic acid to give, after filtration and drying, the title compound: m.p. 189°–193° C.

Analysis for: $C_{22}H_{30}N_2O.2C_2H_2O_4$: Calculated: C, 60.22; H, 6.61; N, 5.40. Found: C, 59.71; H, 6.47; N, 5.40.

B.

N-(Phenylmethyl)-N-[3-[3-(1-piperidinylmethyl)phenoxy]propyl]thieno[3,4-d]isothiazol-3-amine 1,1-dioxide, ethanedioate (1:1)

A neat mixture of 3.38 g (10 mmol) of the free base obtained in A, above, and 2.2 g (10 mmol) of 3-methylthiothieno[3,4-d]isothiazole, S,S-dioxide of Preparation B, supra, is heated to 160° C. under a nitrogen atmosphere for 45 minutes. The mixture is placed under high vacuum and heated (at 160° C.) for an additional 45 minutes.

Upon cooling, the crude product is dissolved in ethanol and treated with oxalic acid. The resulting crude oxalate salt is triturated with ethanol and then methylene chloride to give after drying 1.78 g of the title compound: m.p. 129°–154° C.

Analysis for: $C_{27}H_{31}N_3O_3S_2.C_2H_2O_4$: Calculated C, 58.08; H, 5.55; N, 7.01. Found: C, 57.54; H, 5.64; N, 6.71.

EXAMPLE 2

N-(Phenylmethyl)-N-[3-[3-(1-piperidinylmethyl)phenoxy]propyl]-1,2-benzoisothiazol-3-amine 1,1-dioxide, ethanedioate A solution of 850 mg (2.5 mmol) of the diamine of Example 1A and 500 mg (2.5 mmol) of pseudosaccharyl chloride of Preparation A, supra, in 20 ml of absolute ethanol is heated to reflux and maintained for 30 minutes.

The reaction mixture is then rotoevaporated and partitioned between aqueous sodium bicarbonate and ethyl acetate. The organic phase is dried over magnesium sulfate, filtered and rotoevaporated. The resulting residue is treated with ethanolic oxalic acid to give after filtration and drying the title compound: m.p. 117°–121° C.

Analysis for: $C_{29}H_{33}N_3O_3S.C_2H_2O_4$: Calculated: C, 62.71; H, 5.94; N, 7.50. Found: C, 62.20; H, 5.93; N, 7.21.

EXAMPLE 3

A.
N-[3-[3-(1-piperidinylmethyl)phenoxy]propyl]-1,3-benzodioxole-5-methanamine ethanedioate (1:2)

A mixture of 12.4 g (50 mmol) of 3-[3-[(1-piperidinyl)methyl]phenoxy]propylamine and 7.5 g (50 mmol) of piperonal in 250 ml of benzene is heated to reflux in a Dean-Stark apparatus. When the separation of water is complete the reaction mixture is rotoevaporated to give crude imine.

The crude product is dissolved in 95% ethanol containing 500 mg of 10% palladium on charcoal and hydrogenated at 50 psi in a Parr apparatus. When the uptake of hydrogen has ceased, the mixture is filtered through Celite and rotoevaporated to yield the crude free base of the title compound.

A portion of the free base is treated with ethanolic oxalic acid (2 equivalents) to give after recrystallization from isopropanol, the title compound: m.p. 148°–152° C.

Analysis for: $C_{23}H_{30}N_2O_3.2C_2H_2O_4$: Calculated: C, 57.64; H, 6.09; N, 4.98. Found: C, 57.17; H, 5.99; N, 4.84.

B.
N-(1,3-benzodioxol-5-ylmethyl)-N-[3-[3-(1-piperidinylmethyl)phenoxy]propyl]thieno[3,4-d]isothiazol-3-amine 1,1-dioxide, ethanedioate (1:1)

A mixture of 220 mg (1 mmol) of 3-(methylthio)-thieno[3,4-d]isothiazole 1,1-dioxide of Preparation B, supra, and 383 mg (1 mmol) of the free base of A, above, is heated neat to 160° C. and maintained for 15 minutes.

The crude product is treated with hydrochloric acid and partitioned between aqueous sodium bicarbonate and ethyl ether and then ethyl acetate. The combined organic extracts are dried and rotoevaporated to give crude product. Treatment with ethanolic oxalic acid followed by rotoevaporation and precipitation from acetonitrile with ethyl ether gives 161 mg of the title compound. Recrystallization from ethyl acetate provides a sample: m.p. 96°–101° C.

Analysis for: $C_{28}H_{31}N_3O_5S_2.C_2H_2O_4$: Calculated: C, 55.97; H, 5.17; N, 6.53. Found: C, 55.93; H, 5.41; N, 6.00.

EXAMPLE 4

3-Amino-4-[(1,3-benzodioxol-5-ylmethyl)[3-[3-(1-piperidinylmethylphenoxy]propyl]amino]-3-cyclobutene-1,2-dione, ethanedioate (1:2)

To a solution of 142 mg (1 mmol) of dimethyl squarate in 2 ml of methanol is added dropwise 383 mg (1 mmol) of the free base of Example 3A in 2 ml of methanol. After stirring for 30 minutes, the mixture is treated with excess gaseous ammonia and allowed to stand overnight.

Rotoevaporation affords a non-hygroscopic foam which is subjected to preparative column chromatography on silica gel (gradient elution with methylene chloride:methanol (95:5; 90:10; 80:20)). The free base is converted to the bis-oxalate salt which is precipitated from acetonitrile with ethyl ether to give 101 mg of the title compound: m.p. 102°–109° C.

Analysis for: $C_{27}H_{31}N_3O_5.2C_2H_2O_4$: Calculated: C, 56.61; H, 5.56; H, 6.39. Found: C, 57.08; H, 5.53; N, 6.38.

EXAMPLE 5

The determination of the rate of gastric acid secretion cannot be measured quantitatively with isolated gastric glands or cells. However, the acid secretory response can be monitored semiquantitatively by measuring the uptake of a radiolabelled weak base, $^{14}C$-aminopyrine ($^{14}C$-AP), which accumulates in the glands in proportion to the pH differences between the intraglandular acid compartments and the surrounding medium. The following assay uses this effect in order to measure the ability of the compounds of the invention to inhibit gastric acid secretion by blocking $(H^+ + K^+)$ATPase.

Rat gastric mucosal tissue is collected from 170–220 g male Sprague-Dawley rats. The collected tissues are comminuted with warmed (37° C.) and aerated Pronase E Solution (0.075% in RPMI), placed in water bath at 37° C., aerated with $O_2/CO_2(95/5\%)$ and stirred for 7 minutes. The Pronase E is poured off and the tissues are rinsed in a small amount of DNAse solution (2.5 mg DNAse in 10 ml of Hanks Balanced Salt Solution (HBE) with addition of 1 mg/ml of BSA and 0.76 mg/ml of EGTA). 4 ml of stock DNAse solution is added to 76 ml of HBE and aerated before use. The pH of the solution is adjusted to 7.5 with 2M Tris Buffer. The comminuted tissue is passed through nylon mesh into DNAse solution and incubated at ambient temperature for 20 minutes. The cells obtained thereby are dispersed, filtered through nylon mesh and centrifuged at 1000 RPM's for 7 minutes. The supernatant is discarded and the cells are resuspended in final incubation medium prepared as follows: glucose (108 mg), pyruvic acid (66 mg) and IMX (2.7 mg) are dissolved in 12 ml RPMI-BSA. Immediately before use, 6.1 mg of L-cysteine is dissolved in 5 ml RPMI-BSA. The final incubation medium is (by volume) 80% RPMI-BSA, 10% glucose/PA/IMX solution and 10% L-cysteine solution.

For the actual assay procedure, microfuge tubes are prepared as follows: Into each tube are placed (a) 100 μl of the stimulant dibutyryl cyclic AMP made up in $H_2O$ or an equal volume of distilled $H_2O$;

(b) 100 μl of drug made up in RPMSI-BSA or an equal volume of RPMI-BSA;

(c) 750 μl of the cell suspension; and (d) 50 μl of $^{14}C$-aminopyrine solution.

The tubes are shaken in a 37° C. water bath in a $O_2/CO_2$ (95/5%) atmosphere at about 110 cycles/minute, and incubated for 2 hours. The tubes are then microfuged for 30 seconds, the pellet surface rinsed with 500 μl RPMI-BSA and the cells dispersed in 500 μl distilled $H_2O$. The cells are then transferred to mini-scintillation vials with 5.75 ml of Hydrofluor, vortexed and counted in a Packard liquid scintillation counter.

The inhibition of $^{14}C$-AP uptake is quantified from the scintillation count results and the $IC_{50}$ for test compounds is calculated. The results for some of the compounds of the invention and for the two known $(H^+ + K^+)$ATPase inhibitors, omeprazole and timoprazole, are given in Table I.

TABLE 1

| Compound of Example No. | $(H^+ + K^+)$ ATPase Inhibition ($IC_{50}$) |
| --- | --- |
| 1 | $4 \times 10^{-7}$ M |
| 2 | $1 \times 10^{-7}$ M |
| 3 | $5 \times 10^{-6}$ M |
| 4 | $1 \times 10^{-5}$ M |
| omeprazole | $1 \times 10^{-8}$ M |
| timoprazole | $1 \times 10^{-6}$ M |

The results show that the compounds of the invention exhibit a significant $(H^+ +K^+)$ATPase inhibitory effect.

EXAMPLE 6

The ability of the compounds of the invention to inhibit the spontaneous gastric secretions is examined in the pyloric-ligated ray assay.

Male Charles River SC/CD rats weighing 190–260 gm are fasted for 24 hours with access to tap water ad libitum until the test. Groups of 10 rats each are assigned to either control or drug treatment. Under methahexital anesthesia, a midline laparotomy is performed and a ligature is tightly secured around the pylorus. Either control vehicle (0.25% aqueous methylcellulose) or drug in control vehicle is administered intraduodenally, 1 ml/kg, immediately after ligating the pylorus. The abdominal incision is closed with wound clips and the rats (2 per cage) are allowed to recover from anesthesia. After four hours the rats are sacrificed by $CO_2$ asphyxiation. Their stomachs are removed and the accumulated gastric contents are emptied into graduated tubes. The gastric samples are centrifuged for 10 minutes. Samples contaminated with food or fecal material are discarded.

The volume of gastric juice is recorded and the acid concentration of 1.0 ml sample aliquots is measured by electrometric titration to pH 7.0 using 0.1N sodium hydroxide. Titratable acid output is calculated in microequivalents and the percent inhibition of acid output is calculated as follows:

$$\% \text{ Inhibition of Acid Output} = \frac{\text{Acid Output (control)} - \text{Acid Output (Drug)}}{\text{Acid Output (control)}} \times 100$$

The test results for a compound of the invention and for the known $(H^+ +K^+)$ATPase inhibitors omeprazole and timoprazole, expressed as $ED_{50}$'s, are as follows:

TABLE 2

| Compound of Example No. | Inhibition, $ED_{50}$ (mg/kg) |
| --- | --- |
| 1 | 8 |
| omeprazole | 6 |
| timoprazole | 4 |

The results indicate that the compound tested has significant generalized antisecretory properties.

EXAMPLE 7

The ability of the compounds of the invention to exert a cytoprotective effect is examined in the cold restraint/stress ulcerogenesis assay.

Male Charles River rats weighing between 120–160 gm are deprived of food for 18 hours with water ad libitum. The rats are divided into groups of ten and dosed by the oral route with test compound, 50 mg/kg, or vehicle control, 0.5% carboxymethylcellulose, in a volume of 5 ml/kg. Immediately after dosing, the animals are inserted into aluminum restraining tubes measuring 1⅝ inches in diameter by 8 inches and placed in the cold (4±1° C.). The time in the cold is adjusted so that 90% of the control animals exhibit ulcers. At the end of the test period the animals are killed, the duodenum and esophagus ligated, and the stomach removed. The stomachs are inflated with water, opened along the lesser curvature, spread over the index finger, and the mucosa wiped off to expose the submucosa. The number of hemorrhage sites in the submucosa are counted by visual observation and recorded.

Compounds are reported by determining (A) a percent inhibition which is calculated as follows:

$$\% \text{ inhibition} = \frac{\% \text{ rats with ulcers in control} - \% \text{ rats with ulcers in treatment}}{\% \text{ rats with ulcers in control}} \times 100,$$

or (B) a mean ulcer number ±S.E.M. for each drug treated group and comparing it to that calculated for the control group.

The test results for a compound of the invention and for the known $(H^+ +K^+)$ATPhase inhibitors omeprazole and timoprazole, expressed as $ED_{50}$'s, are as follows:

TABLE 3

| Compound of Example No. | Inhibition, $ED_{50}$ (mg/kg) |
| --- | --- |
| 1 | 6 |
| omeprazole | 12 |
| timoprazole | 8 |

The results indicate that the compound tested exhibits a significant cytoprotective effect.

EXAMPLE 8

The compounds of the invention are tested to determine if they possess any $H_2$-receptor antagonist properties. The assay used involves measurement of the histamine-induced positive chronotropic response in the spontaneously beating right atrium of the guinea pig heart, which is carried out as follows:

A guinea pig right atrium is suspended at 1 g tension (isometric) in a thermostatically controlled (32° C.) tissue bath (10 ml) containing oxygenated (95% $O_2$; 5% $CO_2$) Krebs-Haenseleit buffer (pH 7.4). The tissue is allowed to stabilize over 1 hour. Individual contractions are recorded with a force-displacement transducer through a strain gauge coupler. A control dose-response curve to histamine in the above-described tissue bath is obtained after which the tissue is washed 3 times and allowed to re-equilibrate to basal rate. The test compound is added to the tissue bath at the desired final concentration. Thirty minutes after addition of the compound, a fresh histamine dose response curve is again obtained. Then the response to histamine in the presence of antagonist is compared to the histamine control response. This procedure is repeated, using fresh tissues, for each concentration of antagonist tested. The result is expressed as the apparent dissociation constant ($pA_2$) of the $H_2$ antagonist as determined by standard procedures. Cimetidine is used as the standard for this test.

The compound of Example 1 was inactive in this assay at a level of $1 \times 10^{-6}$M. For comparative purposes, cimetidine, an active $H_2$-receptor antagonist, has a $pA_2$ of 6.5, which is a minimal level of $H_2$-receptor antagonist activity.

What is claimed is:

1. A compund having the formula

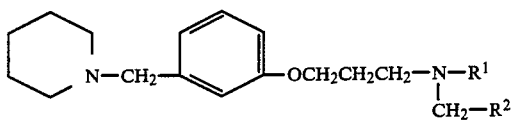

wherein $R^1$ is

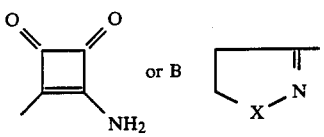 or B wherein B is a moiety having the formula

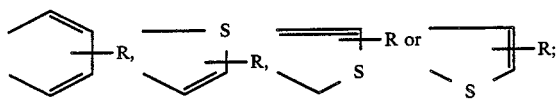

R is H, mono- or dihalo, amino, nitro, cyano, hydroxy, trifluoromethyl, mercapto, lower alkyl, lower alkoxy, alkanoyl of 2 to 5 carbon atoms, lowercycloalkyl, carboxy, alkoxycarbonyl of 2 to 7 carbon atoms, mono- or di-lower alkyl substituted amino, alkanoylamino of 2 to 5 carbon atoms, lower alkyl thio, loweralkylsulfonyl, sulfamoyl, lower alkyl substituted sulfamoyl, phenyl or phenyl substituted with halo, lower alkyl, lower alkoxy, trifluoromethyl, hydroxy, amino, cyano or nitro;

X is $SO_2$, SO, S, or C=O;

$R^2$ is phenyl or 1,3-benzodioxol-5-yl, with the proviso that $R^2$ is phenyl only when $R^1$ is

or a pharmacologically acceptable salt thereof.

2. The compound of claim 1, havingg the name N-(phenylmethyl)-N-[3-[3-(1-piperidinylmethyl)phenoxy]propyl]thieno[3,4-d]isothiazol-3-amine 1,1-dioxide.

3. The compound of claim 1, having the name N-(phenylmethyl)-N-[3-[3-(1-piperidinylmethyl)phenoxy]propyl]-1,2-benzoisothiazol-3-amine 1,1-dioxide.

4. The compound of claim 1, having the name N-(1,3-benzodioxol-5-yl-methyl)-N-[3-[3-(1-piperidinylmethyl)phenoxy]propyl]-thieno[3,4-d]isothiazol-3-amine 1,1-dioxide.

5. The compound of claim 1, having the name 3-amino-4-[(1,3-benzodioxol-5-ylmethyl)[3-[3-(1-piperidinylmethylphenoxy]propyl]amino]-3-cyclobutene-1,3-dione.

* * * * *